US012617817B2

(12) United States Patent
Baileykobayashi et al.

(10) Patent No.: US 12,617,817 B2
(45) Date of Patent: May 5, 2026

(54) CARRIER PEPTIDE FRAGMENT AND USE THEREOF

(71) Applicant: TOAGOSEI CO., LTD., Tokyo (JP)

(72) Inventors: Nahoko Baileykobayashi, Tsukuba (JP); Tetsuhiko Yoshida, Tsukuba (JP)

(73) Assignee: TOAGOSEI CO., LTD., Tokyo (JP)

( * ) Notice: Subject to any disclaimer, the term of this patent is extended or adjusted under 35 U.S.C. 154(b) by 855 days.

(21) Appl. No.: 17/472,310

(22) Filed: Sep. 10, 2021

(65) Prior Publication Data

US 2022/0089641 A1     Mar. 24, 2022

(30) Foreign Application Priority Data

Sep. 14, 2020     (JP) ................................. 2020-153492

(51) Int. Cl.
C07K 7/08          (2006.01)
C12N 5/09          (2010.01)

(52) U.S. Cl.
CPC .............. C07K 7/08 (2013.01); C12N 5/0693 (2013.01)

(58) Field of Classification Search
CPC ................................. C07K 7/08; C12N 5/0693
See application file for complete search history.

(56) References Cited

U.S. PATENT DOCUMENTS

| | | | | |
|---|---|---|---|---|
| 8,603,967 | B2 * | 12/2013 | Yoshida ................... | A61P 25/16 514/1.2 |
| 2010/0183604 | A1 | 7/2010 | Ohta et al. | |
| 2010/0297758 | A1 | 11/2010 | Yoshida et al. | |
| 2012/0122210 | A1 | 5/2012 | Yoshida et al. | |
| 2013/0005034 | A1 | 1/2013 | Yoshida et al. | |

FOREIGN PATENT DOCUMENTS

| | | | | |
|---|---|---|---|---|
| CN | 101778641 | A | 7/2010 | |
| EP | 2236514 | A1 | 10/2010 | |
| JP | 3854995 | B2 | 12/2006 | |
| JP | 5858285 | B2 * | 2/2016 | ....... A61K 47/48323 |
| WO | 2011013700 | A1 | 2/2011 | |
| WO | 2023171820 | A1 | 9/2023 | |

OTHER PUBLICATIONS

Machine translation of JP 5858285B2 on Oct. 3, 2023, pp. 1-16 (Year: 2016).*
Kobayashi N, et. al. Protein Pept Lett. Dec. 2010;17(12):1480-8 (Year: 2010).*
Office Action of corresponding Chinese application CN202111073503. 8, mailing date Jun. 7, 2023; 15 pages with translation.
Goyal P, Pandey D, Siess W. Phosphorylation-dependent regulation of unique nuclear and nucleolar localization signals of LIM kinase 2 in endothelial cells. J Biol Chem. Sep. 1, 2006;281(35):25223-30. doi: 10.1074/jbc.M603399200. Epub Jul. 4, 2006. PMID: 16820362.
Extended European Search Report of corresponding application EP 21196656.9; dated Feb. 22, 2022; 6 pages.
Bohórquez, H.J., Suárez, C.F. & Patarroyo, M.E. Mass & secondary structure propensity of amino acids explain their mutability and evolutionary replacements. Sci Rep 7, 7717 (2017).
Office Action from corresponding application CN 202111073503.8, dated Jun. 29, 2024; 13 pages with translation.
Office Action from corresponding application CN 202111073503.8, dated Apr. 26, 2024; 12 pages with translation.
Kobayashi N, Niwa M, Hao Y, Yoshida T. Nucleolar localization signals of LIM kinase 2 function as a cell-penetrating peptide. Protein Pept Lett. Dec. 2010;17(12):1480-8.
Extended European Search Report of corresponding application EP 21196656.9; dated May 2, 2025; 6 pages.

* cited by examiner

*Primary Examiner* — Marcia S Noble
*Assistant Examiner* — Zanna Maria Beharry

(57)     ABSTRACT

A technology for efficiently introducing a foreign substance into at least cytoplasm of eukaryotic cells from outside the cells is provided. The method for introducing a foreign substance of interest in vitro or in vivo into at least cytoplasm of eukaryotic cells from outside the cells includes (1) a step of preparing a foreign substance introduction construct including a carrier fragment composed of (SEQ ID NO: 1)
KKRTLRKSNRKKR and the foreign substance of interest linked to the N-terminal and/or C-terminal side of the carrier peptide fragment; (2) a step of supplying the foreign substance introduction construct to a sample containing a target eukaryotic cell; and (3) a step of incubating the sample, to which the foreign substance introduction construct has been supplied, to thereby introduce the construct into the eukaryotic cell in the sample.

9 Claims, 1 Drawing Sheet

Specification includes a Sequence Listing.

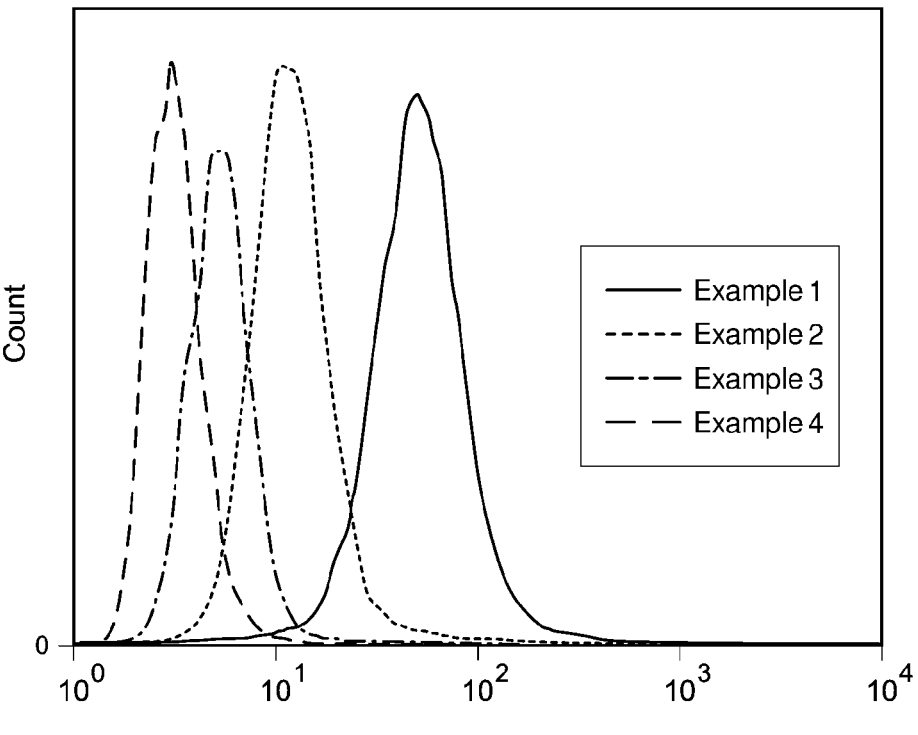

CARRIER PEPTIDE FRAGMENT AND USE THEREOF

CROSS-REFERENCE TO RELATED APPLICATIONS

The present application claims priority on the basis of Japanese Patent Application No. 2020-153492 filed in Japan on Sep. 14, 2020, the entire contents of which are incorporated herein by reference.

REFERENCE TO SEQUENCE LISTING SUBMITTED VIA EFS-WEB

This application includes an electronically submitted sequence listing in .txt format. The .txt file contains a sequence listing entitled "TOAGOSEI CO., LTD." created on Sep. 6, 2021 and is 1,000 bytes in size. The sequence listing contained in this .txt file is part of the specification and is hereby incorporated by reference herein in its entirety.

TECHNICAL FIELD

The disclosure relates to a method of introducing (transporting) a foreign substance into a eukaryotic cell from outside the cell, and to a carrier peptide fragment for use in this method.

BACKGROUND

Conventionally, foreign substances, such as peptides and particularly physiologically active substances, are introduced into the cells of humans and other mammals and the like (eukaryotic cells) to alter the traits of those cells (and moreover tissues and organs composed of such cells) or to improve or enhance the functions of those cells.

For example, Japanese Patent No. 3854995 discloses a cell-penetrating carrier peptide for introducing foreign substances such as polypeptides and DNA into cells. This patent literature describes introducing highly effectively physiologically active substances, such as polypeptides and DNA, into cells by using a carrier peptide conjugate having a cell-penetrating carrier peptide linked to a heterologous polypeptide, DNA or the like.

Methods are also being sought that alter the traits of target cells or improving (or enhancing) their functions by easily introducing whole polypeptides with relatively large molecular weights, as foreign substances (physiologically active substances), into the target cells without using any specialized equipment.

Focusing on specific functions of polypeptides, methods are also being sought that efficiently introduce amino acid sequence parts that are the smallest parts capable of expressing such functions, or in other words, amino acid sequence (foreign substances) constituting peptide motifs (peptide fragments), into cells, instead of introducing whole polypeptides or proteins.

SUMMARY

Meanwhile, WO 2011/013700 describes a foreign substance introduction construct containing a foreign substance of interest together with the amino acid sequence (carrier peptide fragment) of SEQ ID NO:2 (described in Journal of Biological Chemistry, 281(35), 2006, pp. 25223-25230), which is known as a nucleolar localization signal (hereunder called a "NoLS"). This construct can pass highly efficiently through the cell membranes of a eukaryotic cell, whereby the foreign substance of interest can be effectively introduced into the eukaryotic cell from outside the cell.

Cell-penetrating peptides such as the above NoLS have attracted increased interest in recent years from a medical perspective and the like, and there is demand for the development of technologies for more efficiently introducing foreign substances into target cells.

It is an object of the present disclosure, created to meet such demands, to provide a method capable of efficiently introducing a foreign substance of interest into at least the cytoplasm of eukaryotic cells from outside the cells. Another object of the disclosure is to provide a construct including a carrier peptide fragment and a foreign substance of interest and capable of efficiently introducing that foreign substance into the cytoplasm of eukaryotic cells from outside the cells.

To more efficiently introduce the foreign substance introduction construct disclosed in WO 2011/013700 above into the cytoplasm of eukaryotic cells from outside the cells, the inventors substituted various amino acid residues in the amino acid sequence of SEQ ID NO:2 to prepare a construct with greater cell penetrating ability. As a result, the inventors found that cell penetrating ability was improved in a mutant having serine substituted for the $8^{th}$ position asparagine and asparagine substituted for the $9^{th}$ position aspartic acid counting from the N-terminal of the amino acid sequence of SEQ ID NO:2. Surprisingly, substitution of the $9^{th}$ position amino acid residue was not a so-called conservative substitution of amino acid residues (such as substitution of a basic amino acid for another basic amino acid). That is, the amino acid sequence of SEQ ID NO:1 disclosed here was created through extensive trial and error on the part of the inventors.

The method disclosed here is a method of introducing (transporting) a foreign substance of interest into at least the cytoplasm (preferably also into the nucleus) of eukaryotic cells (especially various animal cells such as human and other mammal cells lacking cell walls) from outside those cells (that is, from outside the cell membrane). That is, the foreign substance introduction method disclosed here includes:

(1) a step of preparing a foreign substance introduction construct including a carrier peptide fragment composed of an amino acid sequence below

```
                                        (SEQ ID NO: 1)
                   KKRTLRKSNRKKR
``` and the above foreign substance of interest linked to the N-terminal and/or C-terminal side of the carrier peptide fragment;

(2) a step of supplying the foreign substance introduction construct to a sample containing a target eukaryotic cell; and (3) a step of incubating the sample, to which the foreign substance introduction construct has been supplied, to thereby introduce the construct into the eukaryotic cell in the sample.

Here, a "foreign substance" is an inorganic compound or organic compound capable of binding either directly or indirectly, via a suitable linker, to the N-terminal or C-terminal side of the carrier peptide fragment, and is a substance having a molecular size and chemical properties that allow it the same be introduced into eukaryotic cells.

With the method of introducing a foreign substance of the above configuration, a foreign substance introduction construct constructed by linking a foreign substance of interest (typically an organic compound such as a polypeptide, nucleic acid, dye, drug or the like) directly or indirectly, via a suitable linker, to the N-terminal and/or C-terminal side of the above carrier peptide fragment can be supplied to a sample containing a target eukaryotic cell (such as a culture containing the cell) (i.e., can be added to existing eukaryotic cells) to thereby efficiently introduce the foreign substance of interest from outside the eukaryotic cell (outside the cell membrane) through the cell membrane into the cytoplasm (preferably also into the nucleus through the nuclear envelope).

In a preferred aspect of the foreign substance introduction method disclosed here, the foreign substance is any organic compound selected from the group consisting of polypeptides, nucleic acids, dyes, and drugs. A construct made to contain this kind of organic compound may be efficiently introduced into target cells.

Here, the "polypeptide" here is a polymer having a structure of multiple amino acids linked by peptide bonds. The polypeptide is not limited by the number of peptide bonds (that is, by the number of amino acid residues). That is, the polypeptides include those commonly called peptides composed of about 10 or more but fewer than 300 amino acid residues, and those commonly called proteins (which are high-molecular-weight compounds composed typically of at least 300 amino acid residues). In this field, polypeptides are not strictly separated from proteins. In the present Specification, "polypeptide" is a general term for polymers (including oligomers) composed of multiple amino acid residues.

The term "nucleic acid" means a polymer of nucleotides and encompasses DNA and RNA. The "nucleic acid" is not limited by the number of nucleotides.

In another preferred aspect of the foreign substance introduction method disclosed here, the foreign substance is a mature polypeptide derived from any species of organism, or a precursor polypeptide thereof, and the foreign substance introduction construct is a synthetic polypeptide including an amino acid sequence corresponding to a mature polypeptide or precursor polypeptide thereof as the foreign substance, together with the amino acid sequence of the carrier peptide fragment.

With this configuration, the synthetic polypeptide having the amino acid sequence of the mature polypeptide or precursor polypeptide thereof and the amino acid sequence of the carrier peptide fragment may be efficiently introduced into target eukaryotic cells.

In another preferred aspect of the foreign substance introduction method disclosed here, the amino acid sequence corresponding to the mature polypeptide or precursor polypeptide thereof as the foreign substance is linked to the N-terminal side of the carrier peptide fragment.

With this configuration, the amino acid sequence of the mature polypeptide or precursor polypeptide thereof may be efficiently introduced into target eukaryotic cells.

In another preferred aspect of the foreign substance introduction method disclosed here, the target eukaryotic cell into which the foreign substance introduction construct is introduced is a human or non-human mammalian cell.

With the method disclosed here, the foreign substance may be efficiently introduced into the cytoplasm of a human or non-human mammalian cell.

To achieve the above objects, the disclosure also provides an artificially prepared foreign substance introduction construct for introducing (transporting) a foreign substance of interest into at least cytoplasm (preferably also into the nucleus) of eukaryotic cells (especially various animal cells such as human and other mammalian cells lacking cell walls) from outside those cells (that is, from outside the cell membrane).

That is, the foreign substance introduction construct disclosed here has a carrier peptide fragment composed of (SEQ ID NO: 1)
KKRTLRKSNRKKR and the foreign substance of interest linked to the N-terminal and/or C-terminal side of the carrier peptide fragment.

With the use of this construct, by implementing the foreign substance introduction method disclosed above, a foreign substance of interest may be efficiently introduced into a target eukaryotic cell.

In a preferred aspect of the foreign substance introduction construct disclosed here, as discussed above, the foreign substance is any organic compound selected from the group consisting of polypeptides, nucleic acids, dyes, and drugs.

Preferably the foreign substance is a mature polypeptide derived from any species of organism, or a precursor polypeptide thereof, and the foreign substance introduction construct is a synthetic polypeptide comprising an amino acid sequence corresponding to the mature polypeptide or precursor polypeptide thereof as the foreign substance, together with the amino acid sequence of the above carrier peptide fragment.

More preferably, the amino acid sequence corresponding to the mature polypeptide or precursor polypeptide thereof as the foreign substance is linked to the N-terminal side of the carrier peptide fragment.

BRIEF DESCRIPTION OF THE DRAWINGS

FIG. 1 is a histogram showing the relationship between fluorescent intensity and cell count as obtained by flow cytometry analysis of cells after culture in a test in which a sample 1 including the amino acid sequence of SEQ ID NO:1 and FAM was added (Example 1), a test in which a sample 2 including the amino acid sequence of SEQ ID NO:2 and FAM was added (Example 2), a test in which FAM was added (Example 3) and a test in which only DMSO was added (Example 4), to a culture solution of HeLa cells. Fluorescent intensity is shown on the X axis and cell count on the Y axis.

DETAILED DESCRIPTION

Preferred embodiments of the disclosure are explained below. Matters not specifically mentioned in this Specification that are necessary for implementing the disclosure (such as chemical peptide synthesis methods, cell culture methods, and general matters relating to the preparation of compositions containing peptides and nucleic acids as components) can be understood as design matters by a person skilled in the art based on prior art in the fields of cell engineering, physiology, medicine, pharmaceutics, organic chemistry, biochemistry, genetic engineering, protein engineering, molecular biology, genetics and the like.

Moreover, the disclosure can be implemented based on the contents disclosed in this Specification and technical common knowledge in these fields. In the explanations below, amino acids are sometimes represented by one-letter notation conforming to the nomenclature rules for amino acids shown in the IUPAC-IUB guidelines (but are represented by three-letter notation in the sequence tables). Unless otherwise specified, the term "amino acid residue" in this Specification encompasses the N-terminal amino acid and the C-terminal amino acid of a peptide chain.

In this Specification, a "synthetic peptide" is not a peptide whose peptide chain exists stably by itself in nature, but rather a peptide fragment that has been manufactured by artificial chemical synthesis or biosynthesis (that is, produced based on genetic engineering) and can exist stably in a predetermined composition. "Peptide" here is a term indicating an amino acid polymer having multiple peptide bonds, and the number of amino acid residues therein is not particularly limited.

In the amino acid sequences described in this Specification, the left side is always the N-terminal side, and the right side is the C-terminal side.

The foreign substance introduction construct disclosed here has a carrier peptide fragment composed of

KKRTLRKSNRKKR (SEQ ID NO: 1)

together with the above foreign substance of interest linked to the N-terminal and/or C-terminal side of the carrier peptide fragment.

The "carrier peptide fragment" disclosed here is a sequence defined (understood) by the amino acid sequence of SEQ ID NO:1 and is an amino acid sequence capable of providing cell membrane penetrating ability (more preferably nuclear translocation (nuclear envelope penetrating ability)) in eukaryotic cells.

As discussed above, the amino acid sequence of SEQ ID NO:1 is an amino acid sequence that was discovered by performing various amino acid substitutions in the amino acid sequence of SEQ ID NO:2 to prepare mutants, and then evaluating the cell penetrating ability of the mutants. Specifically, the amino acid sequence of SEQ ID NO:1 is a sequence obtained by substituting serine for the $8^{th}$ position asparagine and asparagine for the $9^{th}$ position aspartic acid in the amino acid sequence of SEQ ID NO:2.

The amino acid sequence of SEQ ID NO:2 is a NoLS corresponding to a partial sequence (motif) including of a total of 13 amino acid residues from the $491^{st}$ amino acid residue to the $503^{rd}$ amino acid residue of LIM kinase 2 (see Journal of Biological Chemistry, 281(35), 2006, pp. 25223-25230), a kind of protein kinase associated with intracellular signaling that is present in human endothelial cells. As described in WO 2011/013700, this partial sequence has excellent cell penetrating ability.

Because the amino acid sequence of SEQ ID NO:1 is a carrier peptide fragment having greater cell penetrating ability than the amino acid sequence of SEQ ID NO:2, a foreign substance introduction construct comprising this carrier peptide fragment together with a foreign substance of interest linked to the N-terminal side and/or C-terminal side of this carrier peptide fragment can be introduced more efficiently into at least the cytoplasm of eukaryotic cells from outside the cells.

Although the "carrier peptide fragment" disclosed here is typically identical to the amino acid sequence of SEQ ID NO:1, it also encompasses modified sequences of this amino acid sequence so long as the cell penetrating ability is not impaired. A "modified sequence" here means an amino acid sequence (modified amino acid sequence) formed by substitution, deletion and/or addition (insertion) of one or more (typically 2 or 3) amino acid residues. Because such a slightly modified sequence can be easily used by a person skilled in the art based on the information disclosed here, it is included in the technical concept of the "carrier peptide fragment" disclosed herein.

Typical examples of the modified sequence in this Specification include sequences obtained by conservative amino acid replacement of 1, 2 or 3 amino acid residues, and sequences obtained by addition (insertion) or deletion of 1, 2 or 3 amino acid residues in the predetermined amino acid sequence. For example, typical examples of conservative amino acid replacement include sequences obtained by substituting a basic amino acid residue for another basic amino acid residue (such as by mutual substitution of a lysine residue and an arginine residue), and sequences obtained by substituting a hydrophobic amino acid residue for another hydrophobic amino acid residue (such as by mutual substitution of a leucine residue, an isoleucine residue, and a valine residue).

The foreign substance introduction construct can be designed and constructed by binding (linking) a desired foreign substance directly or indirectly via a suitable linker to the N-terminal side and/or C-terminal side of this carrier fragment.

The linker is not particularly limited and may be a peptide linker or a non-peptide linker. Although this is not a particular limitation, the amino acid sequence constituting the peptide linker is preferably a flexible amino acid sequence that does not cause steric hindrance. The peptide linker may be for example a linker composed of not more than 10 amino acid residues (more preferably 1 to 5, such as 1, 2, 3, 4, or 5 amino acid residues) including one or two or more amino acid residues selected from glycine, alanine, serine and the like for example. Beta-alanine may also be used as this linker. The non-peptide linker is also not particularly limited, but for example an alkyl linker, PEG (polyethylene glycol) linker, aminohexanoyl spacer or the like may be used.

The foreign substance is typically an organic compound such as a polypeptide, nucleic acid, dye, drug or the like.

The foreign substance may be a polypeptide for example. When the foreign substance is a polypeptide, a peptide chain is designed that includes the amino acid sequence constituting this polypeptide and the amino acid sequence constituting the carrier peptide fragment, and this peptide chain can then by biosynthesized or chemically synthesized to prepare the target foreign substance introduction construct. The foreign substance introduction construct can also be constructed by using various conventionally known scientific methods to link an organic compound that functions as a nucleic acid (such as various kinds of DNA and RNA), a dye (such as various fluorescent dyes including FAM and FITC) or a drug (for example, an antitumor drug containing a nucleic acid antitumor agent such as 5-fluorouracil (5FU), or an antiviral drug such as azidothymidine (AZT)) either directly or indirectly to the N-terminal side and/or C-terminal side of the carrier peptide fragment described above.

The function of the foreign substance is not particularly limited but may be for example promoting induction of stem cell differentiation (stem cell differentiation inducing activity), suppressing tumor cell growth (antitumor activity), suppressing growth of virus-infected cells (antiviral activity) or the like.

The number of foreign substances linked to the carrier peptide fragment in the foreign substance introduction construct is not particularly limited. That is, one or more foreign substance may be linked to one carrier peptide fragment. Although this is not a limitation, for example a polypeptide, nucleic acid, drug or the like may be linked to the N-terminal side and a dye may be linked to the C-terminal side of one carrier peptide fragment. Linking a dye to the carrier peptide fragment is desirable because it makes it easier to evaluate the introduction efficiency of the foreign substance introduction construct into the eukaryotic cell and to evaluate intracellular localization.

When the foreign substance is a polypeptide, the polypeptide (amino acid sequence) used is not particularly limited. For example, a polypeptide with a relatively large number of amino acid residues, such as a polypeptide or protein with about 100 to 1,000 amino acid residues, may be used as the foreign substance.

Typically, the total number of amino acid residues constituting a synthetic polypeptide prepared as an external substance introduction construct is at least several to tens (such as 10), and may suitably be not more than 1,000, or preferably not more than 600, or more preferably not more than 500, or especially not more than 300 (such as 10 to 300). A polypeptide of this length is easy to synthesize (biosynthesize or chemically synthesize) and easy to use.

A mature form or a precursor (including pro-form and prepro-form) of a polypeptide involved in functions such as the development, differentiation, growth, carcinogenesis, homeostasis and metabolic regulation of various cells and tissues (organs) is preferred as the foreign substance. The foreign substance introduction method disclosed here may also be performed to introduce a polypeptide with a previously unknown function into cells and elucidate the function of this polypeptide in cells (biological tissue).

For example, when the eukaryotic cell into which the foreign substance is to be introduced is a stem cell of a human or other mammal, it is desirable to use a mature form or precursor of a polypeptide having various physiological functions associated with differentiation induction of the stem cell. The term "stem cell" encompasses somatic stem cells, embryonic stem cells and induced pluripotent stem cells (hereunder called iPS cells). When the eukaryotic cell into which the foreign substance is to be introduced is a cancer cell (tumor cell), it is desirable to use various polypeptides associated with apoptosis induction in that cancer cell (tumor cell). Alternatively, in this case it may also be desirable to use a polypeptide capable of preventing the cancer cell (tumor cell) from suppressing the function of the immune monitoring mechanism. When the eukaryotic cell into which the foreign substance is to be introduced is a bacteria-infected cell or virus-infected cell, it is desirable to use various polypeptides associated with apoptosis induction in such infected cells, or polypeptides capable of suppressing the growth of bacteria or viruses in such infected cells, or polypeptides capable of preventing bacterial or viral infection from spreading from such infected cells.

Like the carrier peptide fragment, the polypeptide that is the foreign substance may include modified amino acid sequences formed by substitution, deletion and/or addition (insertion) of one or more amino acid residues, so long as the function of the polypeptide is retained.

The foreign substance introduction construct is preferably one in which at least one amino acid residue has been amidated. The structural stability (such as protease resistance) of the foreign substance introduction construct in the cytoplasm and in the nucleus can be improved by amidating a carboxyl group of an amino acid residue (typically the C-terminal amino acid residue of the peptide chain).

For example, when the foreign substance is linked to the N-terminal side of the carrier peptide fragment, it is desirable to amidate the C-terminal amino acid residue of the carrier peptide fragment. On the other hand, when the foreign substance is a polypeptide and this polypeptide is linked to the C-terminal side of the carrier peptide fragment for example, it is desirable to amidate the C-terminal amino acid residue of the polypeptide.

Those foreign substance introduction constructs having relatively short peptide chains (including a polypeptide constructed as a foreign substance, a carrier peptide fragment and a peptide linker) can be easily constructed by ordinary chemical synthesis methods. For example, either a conventionally known solid-phase synthesis method or liquid-phase synthesis method may be adopted. A solid phase synthesis method employing Boc (t-butyloxycarbonyl) or Fmoc (9-fluorenylmethoxycarbonyl) as a protecting group for amino groups is preferred. That is, the above peptide chain having the desired amino acid sequence and modifications (C-terminal amidation, etc.) can be synthesized by solid-phase synthesis using a commercial peptide synthesizer. It is possible to synthesize only part of the peptide chain by these methods, such as only the carrier peptide fragment for example, or a peptide chain that includes the carrier peptide fragment and a peptide linker part.

Alternatively, a peptide part may be synthesized by biosynthesis based on genetic engineering methods. That is, a polynucleotide (typically DNA) is synthesized having a nucleotide sequence (including ATG initiation codon) coding for the desired amino acid sequence. A vector having a gene construct for expression composed of the synthesized polynucleotide (DNA) together with various regulatory elements (including a promoter, ribosome binding site, terminator, enhancer, and various cis-elements for controlling the expression level) for expressing the amino acid sequence in host cells is then constructed according to the host cells.

This recombinant vector is then introduced into host cells (such as yeast, insect, or plant cells) by ordinary techniques, and the host cells or a tissue or organism containing the host cells is cultured under predetermined conditions. The target peptide can thus be produced in cells. The peptide is then separated from the host cells (or from medium if it has been excreted), and refolded, purified and the like as necessary to obtain the target peptide part.

Methods conventionally used in the field may be adopted as the methods for constructing the recombinant vector and introducing the constructed recombinant vector into host cells, and detailed explanations are omitted because these methods themselves are not a particular feature of the disclosure.

For example, a fusion protein expression system can be used for efficient large-volume production in host cells. That is, a gene (DNA) coding for the amino acid sequence of the target polypeptide is chemically synthesized, and this synthetic gene is introduced into a suitable site of a suitable fusion protein expression vector (for example, the pET series provided by Novagen, Inc. or a GST (glutathione S-transferase) fusion protein expression vector such as the pGEX series provided by Amersham Biosciences Corp). Host cells (typically E. coli) are then transformed with this vector. The resulting transformant is cultured to prepare the target fusion protein. Next, this protein is extracted and purified. The resulting purified fusion protein is then cleaved with a predetermined enzyme (protease), and the released target peptide fragment (that is, the designed artificial polypeptide) is collected by a method such as affinity chromatography. The target foreign substance introduction construct (artificial polypeptide) can by constructed using such a conventionally known fusion protein expression system (using for example a GST/His system provided by Amersham Biosciences Corp).

Alternatively, template DNA for a cell-free protein synthesis system (that is, a synthetic gene fragment containing a nucleotide sequence coding for the amino acid sequence of the peptide part of the foreign substance introduction construct) can be constructed, and the target polypeptide can be synthesized in vitro with a so-called cell-free protein synthesis system using various compounds necessary for synthesizing the peptide part (ATP, RNA polymerase, amino acids, etc.). The literature of Shimizu et al for example (Shimizu et al., Nature Biotechnology, 19, 751-755 (2001)) or Madin et al (Madin et al., Proc. Natl. Acad. Sci. USA, 97(2), 559-564 (2000)) may be consulted with respect to cell-free protein synthesis systems. At the time of filing of this application, many companies are already engaged in contract production of polypeptides based on the techniques described in these papers, and cell-free protein synthesis kits are commercially available (from Cell Free Sciences Co., Ltd. in Japan for example).

A single-stranded or double-stranded polynucleotide containing a nucleotide sequence coding for the peptide part of the foreign substance introduction construct and/or a nucleotide sequence complementary to that sequence, can be easily manufactured (synthesized) by conventionally known methods. That is, a nucleotide sequence corresponding to the designed amino acid sequence can be easily determined and provided by selecting codons corresponding to each amino acid residue constituting that amino acid sequence. Once the nucleotide sequence has been determined, a (single-stranded) polynucleotide corresponding to the desired nucleotide sequence can be easily obtained with a DNA synthesizer or the like. The resulting single-stranded DNA can then be used as a template to obtain target double-stranded DNA by various enzymatic synthesis methods (typically PCR). The polynucleotide may be in the form of either DNA or RNA (mRNA or the like). The DNA may be provided as either a double or single stranded. When it is a single strand, it may be a coding strand (sense strand) or a non-coding strand (antisense strand) complementary to the coding strand.

The resulting polynucleotide can then be used as a material for constructing a recombinant gene (expression cassette) for peptide production in various host cells or in a cell-free protein synthesis system as described above.

The foreign substance introduction construct may be used favorably as an active component of a composition for use based on the function of the foreign substance. The foreign substance introduction construct may also be in the form of a salt so long as the function of the foreign substance is not impaired. For example, it can be used in the form of an acid-addition salt, which can be obtained by adding and reacting a commonly used inorganic or organic acid in ordinary methods. Hence, the "foreign substance introduction construct" described in this Specification and Claims includes those in such forms.

The foreign substance introduction construct may also be provided as a composition that may contain various medically (pharmacologically) acceptable carriers suited to the mode of use in addition to the foreign substance introduction construct as an active component.

These carriers are preferably carriers commonly used as diluents, excipients and the like in peptide drugs for example. These carriers may differ appropriately according to the use and form of the foreign substance introduction construct, but typical examples include water, physiological buffers, and various organic solvents. An aqueous alcohol (such as ethanol) solution of a suitable concentration, glycerol, or a non-drying oil such as olive oil or a liposome for example may also be used as a carrier. Examples of accessory components that may be included in medical compositions include various fillers, bulking agents, binders, humectants, surfactants, dyes, perfumes and the like.

The form of the composition is not particularly limited. For example, typical forms include liquids, suspensions, emulsions, aerosols, foams, granules, powders, tablets, capsules, ointments and the like. In the case of an injection or the like, the composition may also be in the form of a freeze-dried product or granules that are dissolved in saline or a suitable buffer (such as PBS) or the like immediately before use to prepare a drug solution.

The processes for preparing drugs (compositions) of various forms from the foreign substance introduction construct (principal component) and various carriers (accessory components) may, in themselves, conform to conventionally known methods, and detailed explanations are omitted because these preparation methods themselves are not a feature of the disclosure. Detailed information about formulations is described for example in Comprehensive Medicinal Chemistry, Corwin Hansch Ed., Pergamon Press (1990).

A method of using the foreign substance introduction construct (composition) to introduce the foreign substance introduction construct either in vivo or in vitro is provided. This method generally includes the following steps:

a step of preparing a foreign substance introduction construct comprising a carrier peptide fragment composed of the amino acid sequence of SEQ ID NO:1 together with the foreign substance of interest linked to the N-terminal and/or C-terminal side of the carrier peptide fragment, a step of supplying the foreign substance introduction construct to a sample containing a target eukaryotic cell, and a step of incubating the sample to which the foreign substance introduction construct has been supplied to thereby introduce the construct into the eukaryotic cell in the sample.

In vivo, the "eukaryotic cell" may encompass for example various tissues, organs, blood, lymph and the like. In vitro, it may encompass various cell masses, tissues, organs, blood and lymph extracted from living organisms, as well as cell lines and the like.

A composition containing the construct disclosed above can be used in vivo by a method and in a dosage suited to the form and object of the composition. For example, in liquid form it may be administered by intravenous, intramuscular, subdermal, intradermal, or intraperitoneal injection in the desired dose to an affected area (such as a malignant tumor tissue, virus-infected tissue, inflamed tissue or the like) of a patient (that is, a living organism). In a solid form such as a tablet or a gel or aqueous jelly form such as an ointment, it can also be administered directly to a desired tissue (that is, an affected area such as a tissue or organ containing tumor cells, virus-infected cells, inflamed cells or the like). It can also be administered orally in a solid form such as a tablet. In the case of oral administration, it is desirable to use a capsule or protective material (coating) to prevent degradation by digestive enzymes in the digestive tract.

In the case of eukaryotic cells cultured in vitro, a suitable amount of the composition disclosed here (that is, a suitable amount of the foreign substance introduction construct) may also be supplied at least once to a culture solution of the target eukaryotic cells. The amount supplied each time and the number of administrations is not particularly limited because they may differ according to conditions such as the type of eukaryotic cell being cultured, the cell density (cell density at beginning of culture), number of passages, culture conditions, type of medium and the like. For example, the composition is preferably added once, twice, or more than twice so that the density of the carrier peptide fragment in the culture solution is about 0.05 μM to 100 μM, or about 0.5 μM to 50 μM for example, or about 1 μM to 20 μM for example.

One example of an introduction method in vitro is given in the examples below.

The method of evaluating the introduction efficiency of the foreign substance introduction construct is not particularly limited. For example, when a dye (typically a fluorescent dye compound) is linked to the construct, the introduction efficiency into eukaryotic cells can be evaluated by microscope observation (such as fluorescent microscope observation), flow cytometry or the like. The introduction efficiency of the construct can also be evaluated by immunochemical methods (such as Western blot or immune cell staining) using an antibody that specifically recognizes the peptide part of the construct.

Certain examples of the technology disclosed here are explained below, but not with the intention of limiting the technology disclosed here to what is shown in these examples.

Preparation of Foreign Substance Introduction Construct

The two synthetic peptides (peptide 1 and peptide 2) shown in Table 1 were prepared. Peptide 1 is a carrier peptide fragment composed of the amino acid sequence represented by SEQ ID NO:1. Peptide 2 is a peptide composed of the amino acid sequence represented by SEQ ID NO:2, and this amino acid sequence is known as a NoLS of LIM kinase 2.

Both peptide 1 and peptide 2 were synthesized with the carboxyl group (—COOH) of the C-terminal amino acid residue amidated (—CONH$_2$). Both peptide 1 and peptide 2 were synthesized by solid-phase synthesis (Fmoc method) using a commercial synthesizer in accordance with the manual.

Detailed explanations are omitted because the mode of use of the peptide synthesizer is not in itself a feature of the disclosure.

TABLE 1

| Peptide No. | Sequence | SEQ ID NO |
|---|---|---|
| 1 | KKRTLRKSNRKKR | 1 |
| 2 | KKRTLRKNDRKKR | 2 |

Next, the fluorescent dye FAM (C$_{21}$H$_{12}$O$_7$: 5(6)-carboxyfluorescein, molecular weight 376.3, excitation wavelength 495 nm, fluorescent wavelength 520 nm) was linked directly as a foreign substance by ordinary methods to the amino acid residues at the N-terminals of the peptide 1 and peptide 2 to prepare a foreign substance introduction construct having the peptide 1 (also called "sample 1") and a foreign substance introduction construct having the peptide 2 (also called "sample 2"). The sample 1 and sample 2 were each diluted with DMSO to prepare a sample solution 1 with a sample 1 concentration of 2 mM and a sample solution 2 with a sample 2 concentration of 2 mM.

Evaluating Cell Penetrating Ability of Sample 1 and Sample 2

The cell penetrating ability of sample 1 and sample 2 was evaluated using HeLa cells (cell line established from human cervical cancer cells). In Table 2, Example 1 indicates a test of addition of sample 1 to a culture solution of HeLa cells, Example 2 indicates a test of addition of sample 2, Example 3 indicates a test of addition of FAM diluted with DMSO, and Example 4 indicates a test of addition of DMSO only.

TABLE 2

| | Additive |
|---|---|
| Example 1 | FAM-KKRTLRKSNRKKR-CONH$_2$ |
| Example 2 | FAM-KKRTLRKNDRKKR-CONH$_2$ |
| Example 3 | FAM |
| Example 4 | None (DMSO only) |

Example 1

HeLa cells were cultured in an ordinary culture medium, DMEM (Dulbecco's modified Eagle's medium, manufactured by Fuji Film Wako Pure Chemical Industries, Cat. No. 043-30085) containing 10% FBS (fetal bovine serum).

HeLa cells adhering to the culture plate were washed with PBS, 0.25% trypsin/EDTA solution was added, and the cells were incubated for 3 minutes at 37° C. After incubation, the same DMEM medium containing 10% FBS was added to deactivate the trypsin, and the cells were precipitated by 5 minutes of centrifugation at 150×g. The supernatant produced by centrifugation was removed, and the same DMEM containing 10% FBS was added to the precipitate (cell pellet) to prepare an approximately 1×10$^5$ cells/mL cell suspension. 2 mL of the cell suspension was added to the wells of a commercial 6-well plate (Iwaki microplate commercially available from AGC techno glass Co., Ltd) to seed the cells at a rate of approximately 2×10$^5$ cells/well. This was then cultured for 3 hours at 37° C. under conditions of 5% CO$_2$, causing the cells to adhere to the bottom of the wells. Because the cell penetrating ability evaluation is performed in triplicate, cells were seeded in 3 wells for the test of Example 1, and the following operations were performed on each well.

Next, the above 2 mM sample solution 1 was diluted with the above DMEM containing 10% FBS to prepare a sample solution 1 in which the concentration of the sample 1 was 20 μM. 1 mL of the culture supernatant was removed from each well after the 3 hours of culture, and 1 mL of 20 μM sample solution 1 was added to the well so that the sample 1 concentration of the culture solution in the well was 10 μM and the DMSO concentration was 0.5%. This was then incubated for 20 hours at 37° C. under conditions of 5% CO$_2$. After this 20-hour incubation, the culture supernatant was removed from the well, and the cells in the well were washed twice with 1 mL of PBS. 200 μL of 0.25% trypsin/EDTA solution was then added to the well, and the cells were incubated for 3 minutes at 37° C. After this incubation, 400 μL of the above DMEM containing 10% FBS was added to the well to deactivate the trypsin, after which the cell suspension in the well was transferred to a tube, and the cells were collected. 600 μL of PBS was then added to each well to wash the well. The PBS in the well was then transferred to the above tube to collect the cells remaining in the well in the tube. This tube was centrifuged for 5 minutes under conditions of 210×g at 4° C. After centrifugation the supernatant was removed, and the precipitate (cell pellet) was suspended (washed) in 1 mL of PBS and centrifuged under the same conditions. This operation was repeated twice to remove the supernatant and obtain cells (a cell pellet) that had been cultured in medium containing the sample 1.

The cells (cell pellet) obtained above were analyzed by flow cytometry to assess the cell penetrating ability of the sample 1. A flow cytometer (On-Chip Biotechnologies Co., Ltd.) was used for the analysis.

The cell pellet obtained above was suspended in 50 μL of PBS for purposes of this analysis. A further 50 μL of 2× sample buffer for flow cytometry was added to this suspension to prepare a cell suspension for analysis.

Gating was performed with the flow cytometer based on forward scatter (FSC) and side scatter (SSC), a gate was set for the cell population under analysis, and the cell population within this gate was measured for fluorescent intensity. Analysis was performed so that the cell population composed of at least 5,000 cells. Fluorescent intensity was measured with the fluorescence detector FL2 of the flow cytometer, which can detect the fluorescent wavelength of FAM. These measurement results were analyzed with commercial analysis software (FlowJo™, TreeStar Co.) which enables single-cell flow cytometry to obtain the mean fluorescent intensity (MFI) of the measured cell population.

Example 2

The operations were the same as in Example 1 except that the sample solution 2 was used instead of the sample solution 1.

Example 3

The operations were the same as in Example 1 except that a FAM solution diluted with DMSO was used instead of the sample solution 1. The concentration of this FAM solution was the same as the concentration of the sample solution 1 (that is, the culture solution in each well had a FAM concentration of 10 μM and a DMSO concentration of 0.5%).

Example 4

The operations were the same as in Example 1 except that DMSO was used instead of the sample solution 1.

The results from Examples 1 to 4 are shown in Table 3 and FIG. 1. The average of MFI values in triplicate is given in each example. FIG. 1 shows a flow cytometry histogram using the test examples closest to the average MFI value among values in triplicate in each example.

TABLE 3

|  | Example 1 | Example 2 | Example 3 | Example 4 |
|---|---|---|---|---|
| MFI | 62 | 15.5 | 6 | 3.4 |

As shown in FIG. 1, in the case of the Example 1 involving addition of a foreign substance introduction construct 1 having the peptide 1 and a fluorescent dye (FAM) and the Example 2 involving addition of a foreign substance introduction construct 2 having the peptide 2 and a fluorescent dye (FAM), the histogram was shifted to the right on the X-axis in comparison with the Example 3 in which only FAM was added, confirming that a fluorescent dye (FAM) as a foreign substance was introduced more efficiently into the cytoplasm of HeLa cells using the peptide 1 and peptide 2. Comparing Examples 1 and 2, moreover, the histogram is shifted more to the right on the X-axis in Example 1 than in Example 2, confirming that the foreign substance introduction construct having the peptide 1 has greater cell penetrating ability than the foreign substance introduction construct having the peptide 2, and can introduce a foreign substance into cells from outside the cells with greater efficiency. Comparing the MFI values in Table 3, the efficiency (cell penetrating ability) was confirmed to be 4 times higher in Example 1 than in Example 2.

Although detailed data are not shown, the inventors' research has shown that even if the foreign substance is a polypeptide, a nucleic acid or a drug rather than a fluorescent dye, this foreign substance is introduced efficiently from outside the cell through the cell membrane into at least the cytoplasm.

As shown above, with the technology disclosed here a method of introducing a foreign substance of interest into at least the cytoplasm of eukaryotic cells from outside the cells is provided as one especially preferred aspect of the foreign substance introduction method, and this method is characterized by using a carrier peptide fragment composed of SEQ ID NO:1. This carrier peptide fragment is suited to the goal of introducing a foreign substance of interest into cytoplasm.

Detailed examples of the technology disclosed here were disclosed above, but the scope of the Claims is not limited thereby. The technology described in the Claims encompasses various changes and modifications to the specific examples given above.

The technology disclosed here provides an artificially prepared construct for introducing a foreign substance of interest into the cytoplasm of eukaryotic cells from outside the cells (especially various animal cells such as human and other mammal cells lacking cell walls). Using this construct, a foreign substance of interest can be introduced effectively into target cells to obtain cells having the introduced foreign substance and an organ or biological tissue containing the cells having the foreign substance. This construct can also be used to provide a drug for a disease.

Sequence Table Free Text

SEQ ID NOS:1 to 2 Synthetic peptides

---

What is claimed is:

1. A method of introducing a foreign substance of interest into at least cytoplasm of eukaryotic cells from outside the cells, the method comprising:

(1) a step of preparing a foreign substance introduction construct including a carrier peptide fragment composed of the amino acid sequence below (SEQ ID NO: 1)
           KKRTLRKSNRKKR and the foreign substance of interest linked to the N-terminal and/or C-terminal side of the carrier peptide fragment;

(2) a step of supplying the foreign substance introduction construct to a sample containing a target eukaryotic cell; and (3) a step of incubating the sample, to which the foreign substance introduction construct has been supplied, to thereby introduce the foreign substance introduction construct into the eukaryotic cell in the sample.

2. The method according to claim 1, wherein the foreign substance is any organic compound selected from the group consisting of polypeptides, nucleic acids, dyes, and drugs.

3. The method according to claim 2, wherein the foreign substance is a mature polypeptide derived from any species of organism, or a precursor polypeptide thereof, and the foreign substance introduction construct is a synthetic polypeptide comprising an amino acid sequence corresponding to a mature polypeptide or precursor polypeptide thereof as the foreign substance, together with the amino acid sequence of the carrier peptide fragment.

4. The method according to claim 3, wherein the amino acid sequence corresponding to the mature polypeptide or precursor polypeptide thereof as the foreign substance is linked to the N-terminal side of the carrier peptide fragment.

5. The method according to claim 1, wherein the target eukaryotic cell into which the foreign substance introduction construct is introduced is a human or non-human mammalian cell.

6. A foreign substance introduction construct prepared for introducing a foreign substance of interest into at least cytoplasm of eukaryotic cells from outside the cells, the foreign substance introduction construct comprising: a carrier peptide fragment composed of KKRTLRKSNRKKR (SEQ ID NO: 1), and the foreign substance of interest linked to the N-terminal and/or C-terminal side of the carrier peptide fragment.

7. The construct according to claim 6, wherein the foreign substance is any organic compound selected from the group consisting of polypeptides, nucleic acids, dyes, and drugs.

8. The construct according to claim 7, wherein the foreign substance is a mature polypeptide delivered from any species of organism, or a precursor polypeptide thereof, and the construct is a synthetic polypeptide comprising an amino acid sequence corresponding to the mature polypeptide or precursor polypeptide thereof as the foreign substance, together with the amino acid sequence of the carrier peptide fragment.

9. The construct according to claim 8, wherein the amino acid sequence corresponding to the mature polypeptide or precursor polypeptide thereof as the foreign substance is linked to the N-terminal side of the carrier peptide fragment.

* * * * *

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
```

-continued

```
<223> OTHER INFORMATION: synthetic peptide

<400> SEQUENCE: 1

Lys Lys Arg Thr Leu Arg Lys Ser Asn Arg Lys Lys Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: synthetic peptide

<400> SEQUENCE: 2

Lys Lys Arg Thr Leu Arg Lys Asn Asp Arg Lys Lys Arg
1               5                   10
```